(12) United States Patent
Kavallieratos et al.

(10) Patent No.: US 8,906,694 B2
(45) Date of Patent: Dec. 9, 2014

(54) ORGANOMETALLIC FLUORESCENT SENSORS FOR NITRIC OXIDE DETECTION AND IMAGING

(71) Applicant: The Florida International University Board of Trustees, Miami, FL (US)

(72) Inventors: Konstantinos Kavallieratos, Miami, FL (US); Nikolaos M. Tsoukias, Miami, FL (US); Lissette I. Lozano-Lewis, San Miguel (PE)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 13/850,572

(22) Filed: Mar. 26, 2013

(65) Prior Publication Data

US 2013/0252273 A1 Sep. 26, 2013

Related U.S. Application Data

(60) Provisional application No. 60/615,623, filed on Mar. 26, 2012.

(51) Int. Cl.
*G01N 33/52* (2006.01)
*C12Q 1/02* (2006.01)

(52) U.S. Cl.
USPC .............................. 436/119; 556/137; 435/29

(58) Field of Classification Search
USPC .............................. 436/116; 556/137; 435/29
See application file for complete search history.

(56) References Cited

U.S. PATENT DOCUMENTS

| | | | |
|---|---|---|---|
| 7,494,821 B2 | 2/2009 | Lippard et al. | |
| 7,618,997 B2 | 11/2009 | Nagano et al. | |
| 2003/0068275 A1* | 4/2003 | Lippard et al. | 424/9.36 |

OTHER PUBLICATIONS

Hu et al., A copper(II) rhodamine complex with a tripodal ligand as a highly selective fluorescence imaging agent for nitric oxide. Chem. Commun., 2011, 47, 11507-11509.
Kavdia et al., A model of Nitric Oxide diffusion in an arteriole: impact of hemoglobin based blood substitutes. American Journal of Physiology 2002, 282(6):H2245-53.
Kojima et al., Detection and Imaging of Nitric Oxide with Novel Fluorescent Indicators: Diaminofluoresceins. Anal. Chem., 1998, 70, 2446-2453.
Kojima et al., Fluorescent Indicators for Imaging Nitric Oxide Production. Agnew. Chem. Int. Ed. Engl., 1999, 38, 3209-3212.
Lim et al., Visualization of nitric oxide in living cells by a copper-based fluorescent probe. Nature Chem Biol., 2006, 2, 375-380.
Madrasi et al., Glutathiyl radical as an intermediate in glutathione nitrosation Free Radical Biology and Medicine, 2012, 53, 1968-1976.
Moncada et al., The L-Arginine-Nitric Oxide Pathway. N. Engl. J. Med., 1993, 329, 2002-20012.
Namin et al., Kinetic Analysis of DAF-FM activation by NO; toward calibration of a NO-sensitive fluorescent dye. Nitric Oxide: Biology and Chemistry, 2013, 28, 39-46.
Pluth et al., Cell-Trappable fluorescent probes for nitric oxide visualization in living cells. Org. Lett. 2010, 12, 2318-2321.
Snyder et al., Biological roles of nitric oxide. Sci Am. 1992, 266, 68-77.
Tsoukias et al., A model of nitric oxide capillary exchange. Microcirculation 2003, 10(6): 479-95.
Tsoukias et al., A theoretical model of nitric oxide transport in arterioles: frequency vs amplitude dependent control of cGMP formation. American Journal of Physiology 2004, 286(3): H1043-56.
Tsoukias et al., Erythrocyte consumption of Nitric Oxide in the presence and absence of plasma-based Hemoglobin. American Journal of Physiology 2002, 282(6):H2265-77.
Tsoukias, Nitric Oxide bioavailability in the microcirculation: Insights from mathematical models. Microcirculation 2008, 15, 8.
Tuteja et al., Nitric Oxide as a Unique Bioactive Signaling Messenger in Physiology and Pathophysiology. J. Biomed. Biotechnol., 2004, 4, 227-237.
Yuan et al., Development of a ratiometric fluorescent sensor for ratiometric imaging of endogenously produced nitric oxide in macrophage cells. Chem. Commun., 2011, 47, 9372-9374.

* cited by examiner

*Primary Examiner* — Rosanne Kosson
(74) *Attorney, Agent, or Firm* — Marshall, Gerstein & Borun LLP

(57) ABSTRACT

Disclosed herein are methods of detecting the presence and/or concentration of nitric oxide using organometallic complexes and changes in fluorescence.

29 Claims, 4 Drawing Sheets

ORGANOMETALLIC FLUORESCENT SENSORS FOR NITRIC OXIDE DETECTION AND IMAGING

CROSS REFERENCE TO RELATED APPLICATIONS

The benefit of U.S. Provisional Application No. 61/615,623, filed Mar. 26, 2012 is claimed, the disclosure of which is incorporated by reference in its entirety.

STATEMENT OF U.S. GOVERNMENT SUPPORT

This invention was made with government support under Grant Number SC1-HL95101, awarded by the National Institutes of Health. The government has certain rights in the invention.

BACKGROUND

Nitric oxide (NO) has several functions of particular importance to human health [1,2]. It is now recognized as a key signaling molecule in the cardiovascular system [3]. NO has a central role in diverse pathological conditions, such as hypertension, ischemic heart disease, and stroke. There is an increased effort today aimed at the development of therapeutic and diagnostic products based on the new knowledge on NO. The importance of this field was highlighted with the 1998 Nobel Prize in medicine and physiology for their NO related research.

Despite significant scientific contributions in the field NO fluorescence detection [3-5], the development of novel dyes that are ratiometric and address some significant concerns with prior systems will not only provide practical alternatives for detection of this all important molecule in human physiology but also provide answers to fundamental questions about basic physiological functions of NO, which still remain. Over the last decade, NO-dependent signaling in the cardiovascular system has been modeled [6-9]; controversies regarding the role of NO in the vasculature have been reviewed [10]; as has reactivity of NO with biologically important thiols [11]. This work highlights the need for radically improved ways to assess one of the most important molecules for human physiology. Regretfully, quantification of NO in tissues remains a challenge due to the absence of a detection method that can combine significant spatial and temporal resolution with high NO specificity [12]. Indeed the current art for NO detection, which is the DAF-FM dye is non-ratiometric, has several shortcomings, and its reactivity with NO has recently become the subject of controversy [13]. These problems with existing technology for NO detection have led to intense efforts worldwide for developing new dyes for NO detection that operate by different mechanisms [4, 14-16].

SUMMARY

Disclosed herein are methods of detecting nitric oxide in a sample. The sample can have NO in a concentration of less than 1 μM, 0.1 μM to 2000 μM, or 2000 μM more. The methods provided herein can detect NO or measure the amount of NO in the sample. In some embodiments, the method provides an absolute measurement of the amount of NO in the sample (or the NO concentration). The sample can comprise cells. The method can be used to determine the intracellular NO concentration or activity, the extracellular NO concentration or activity, or both.

Thus, provided herein are methods of detecting nitric oxide (NO) in a sample comprising contacting the sample with a complex of formula (I) or (II):

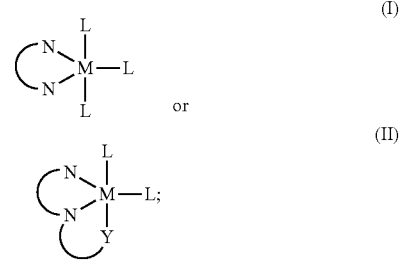

and measuring a fluorescence of the resulting mixture, wherein a change in fluorescence after contact with the sample, compared to the fluorescence of the complex of formula (I) or (II) in the absence of the sample, indicates the presence of NO in the sample, wherein M is a transition metal; each L is a ligand independently selected from CO, tetrahydrofuran (THF), triflate, alkoxide, nitrate, nitrito, chloro, sulfate, amine, phosphine, phosphite, pi-bound alkene, alcohol, ketone, ether, thiol, thioether, nitrile, isonitrile, amide, thioamide or a solvent; N—N is a bidentate nitrogen containing ligand; N—N—Y is a tridentate nitrogen containing ligand and Y is a metal-coordinating moiety. In some cases, M is selected from Re, Ru, Os, Ir, Mn, Tc, Fe, Ru, Co, Rh, Ni, Pd, Pt, Cu, Cr, Mo, W, V, Nb, and Ta. In various cases, M is selected from Re(I), Ru(II), Os(II), and Ir(III). In various cases, at least one L is CO. In some cases, one L is triflate. In some cases, one L is THF. In various cases, one L is triphenylphosphine or triethylamine. In some cases, at least two L are CO. In various cases, the bidentate ligand comprises phenanthrolinyl, dipyridophenazinyl, or bipyridyl, and can be substituted or unsubstituted. In various cases, the tridentate ligand comprises phenanthrolinyl, dipyridophenazinyl, or bipyridyl substituted with a metal-coordinating moiety or a weakly coordinating fluorophore ("WCF"). The WCF can be triazoyl or dansyl, or can be a moiety as described in detail below. The complex can be selected from the group consisting of Re(phen)(CO)$_2$(THF)(CF$_3$SO$_3$); Re(phen)(CO)$_2$(PPh$_3$)(CF$_3$SO$_3$); and Re(phen)(CO)$_2$(Et$_3$N)(CF$_3$SO$_3$). In various cases, the complex has a structure of formula (I) further comprising a fourth L resulting in a complex of formula (III):

In some cases, the complex has a structure of formula (II) further comprising a third L, resulting in a complex of formula (IV):

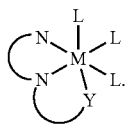

(IV)

In various embodiments, the change in fluorescence is correlated to the concentration of the NO in the sample. In some cases, an emitted fluorescence intensities ratio at two wavelengths, following excitation at a third wavelength can be correlated to the NO concentration in the sample. In various cases, an emitted fluorescence intensities ratio at one wavelength, following alternate excitation at a second and third wavelength, can correlated to the NO concentration in the sample. In various cases, the measurement is carried out by using an excitation light having a wavelength of 280 nm or higher.

DETAILED DESCRIPTION

Figure 1:
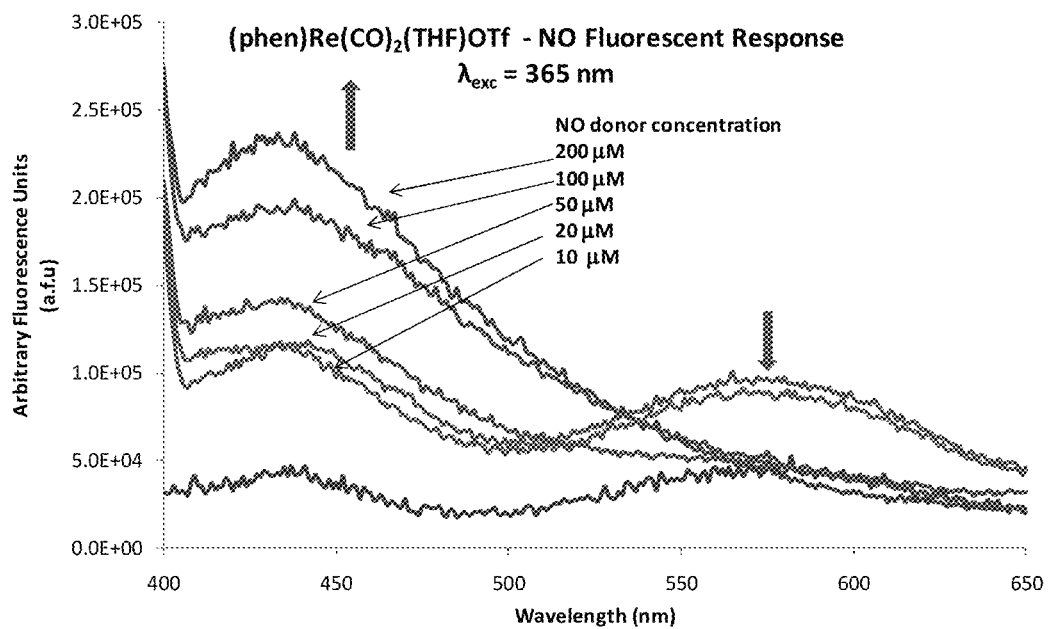
FIG. 1 shows the fluorescent ratiometric response to a prototype NO sensor (spectra).

In order to achieve a ratiometric fluorescent probe that can detect changes in NO concentration with high sensitivity and selectivity, an entirely new approach on NO sensing is employed that combines the following elements: 1) NO binding to a metal center, such as Re(I), Ru(II), Os(II), and Ir(III), among other metals; 2) a bidentate or tridentate phenathroline (phen), dipyridophenazine (dppz), or 2,2'-bipyridine (bipy) framework attached on the metal, which provides favorable photophysical characteristics, as well potential for modification, for fine-tuning the emission wavelength and also for addition of Weakly Coordinated Fluorophores (WCF).

WCF can be attached to the bi- or tri-dentate ligand via any means known to the ordinarily skilled artisan. Some specific examples of WCF contemplated include triazolyl and dansyl. Other examples of WCF include 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 488 hydrazide-water, Allophycocyanin pH 7.5, AMCA conjugate, Amino Coumarin, APC (allophycocyanin), Atto 647, BCECF pH 5.5, BCECF pH 9.0, Carboxynaphthofluorescein pH 10.0, Cascade Blue, Cascade Blue BSA pH 7.0, Cascade Yellow, Citrine, Coumarin, Cy 2, Cy 3, Cy 3.5, Cy 5, Cy 5.5, Dansyl Cadaverine, Dansyl Cadaverine, DAPI, Dapoxyl(2-aminoethyl)sulfonamide, DDAO pH 9.0, Di-8 ANEPPS, DsRed, DTAF, dTomato, Eosin, Erythrosin-5-isothiocyanate pH 9.0, Ethidium Bromide, Ethidium homodimer, FITC, FlAsH, Fluo-3, Fluo-3 Ca2+, Fluo-4, Fluor-Ruby, Fluorescein, Fluorescein 0.1 M NaOH, Fluorescein dextran pH 8.0, Fluorescein pH 9.0, Fluoro-Emerald, FM 1-43, FM 4-64, Fura Red Ca2+, Fura Red, high Ca, Fura Red, low Ca, Fura-2 Ca2+, Fura-2, high Ca, Fura-2, no Ca, HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, NBD-X, Nile Blue, Nile Red, Nissl, Oregon Green 488, Oregon Green 514, Pacific Blue, Phycoerythrin, PO-PRO-1, PO-PRO-3, POPO-1, POPO-3, Propidium Iodide, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodaminen Green pH 7.0, Sodium Green Na+, Sulforhodamine 101, EtOH, SYBR Green I, SYPRO Ruby, Tetramethylrhodamine dextran pH 7.0, TRITC, and X-Rhod-1 Ca2+.

Re(I) and Ru(II) complexes have been used as fluorescent sensors for other targets, and photoluminescence applications. Their favorable photochemical properties, stability of NO complexes, and flexibility in accommodating conjugated ligand systems offer potent platforms for the design of novel NO-selective dyes.

In some embodiments, methods of detecting NO comprise metal photoluminescent complexes of 2,2'-bipyridine (bipy), phenanthroline (phen), and dipyridophenazine (dppz) derivatives and their substituted analogs, complexed to a transition-metal, such as Re(I), Ru(II), Os(II), or Ir(III) (compound 1 in Scheme 1) which are transformed thermally or photochemically to reactive precursors (2) that contain a labile ligand (S), such as tetrahydrofurane (THF) or a coordinating organic solvent, which generate a ratiometric response upon NO reaction with the activated complex and subsequent chemical transformation. The labile ligand S can be a phosphine (such as PPh$_3$), an amine (such as a trialkyl amine, e.g., Et$_3$N), a ketone, an alcohol, an ether, an isonitrile or nitrile (such as CH$_3$CN) or other ligand that can easily be displaced upon NO reaction, or activate the molecule for reaction with NO.

Scheme 1

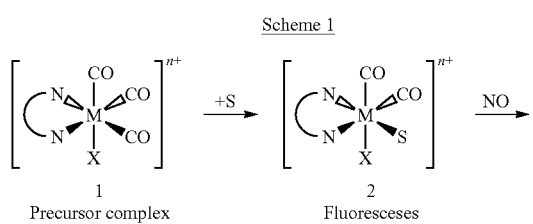

1
Precursor complex

2
Fluoresceses

M = Metal (incl. Re(I), Ru(II), Os(II), and Ir(III))
S = Weakly bound ligand (such as THF)
X = X-type ligand i.e $CF_3SO_3^-$
N⌒N = 1,10-phenanthroline, dipyridophenazine, or 2,2′ bipy analog with extensive conjugation
n = 0, for Re(I), +1 for Ru(II) and Os(II), +2 for Ir(III)

Alternative formulations for 3 depending on metal configuration:

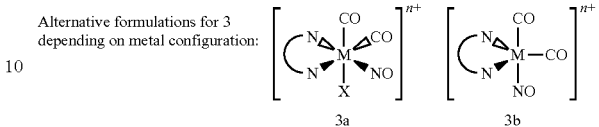

3a    3b

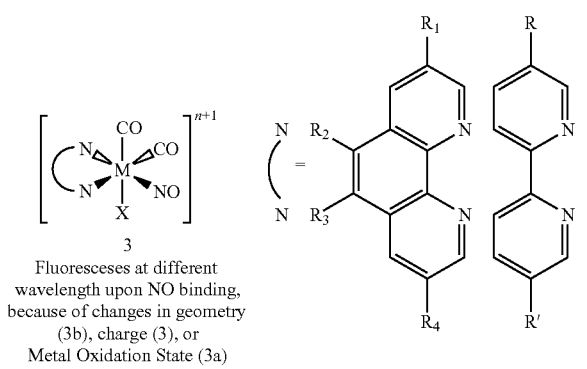

3
Fluoresceses at different wavelength upon NO binding, because of changes in geometry (3b), charge (3), or Metal Oxidation State (3a)

The change in the fluorescence emission wavelength may be the result of changes in the complex geometry (3b), overall charge on the complex (3), or metal oxidation states (3a), dependent on the specific metal, and resulting complex formulations (refer to 3, 3a and 3b in Scheme 1). NO detection can also be achieved based on the reaction of NO with the complexed phen, bupy, or dppz moiety, which is activated for reacting with NO in the presence of the metal. The alteration of overall charge in the products (such as complex 3) provides opportunities for a trappable charged complex, comparable in trapability to the hydrolyzed esters of DAF-FM, a currently available NO detector.

In various embodiments, transition metal photoluminescent complexes of functionalized bipyridine and phenanthroline derivatives, containing additional fluorophores, such as dansyl (dns) or triazole as some examples, in direct conjugation to a phen or bipy framework can be synthesized to generate ratiometric responses upon NO binding, due to a loss-of-conjugation blue shift, which result in emission of the sensor at a different wavelengths than the uncomplexed dye (Scheme 2).

Scheme 2

Fluoresceses → NO → Fluoresceses at different wavelength due to loss of conjugation upon NO binding WCF = Weakly coordinated fluorophore (triazole, dansyl)
N⌒N = 1,10-phenanthroline or 2,2′ bipyridine directly conjugated to WCF
Y = coordinating atom containing a lone pair, which is part of the extended ligand N—N—Y These platforms provide a sensor for NO detection in biological tissues that is based on a novel concept, and provides the benefit of reduced cost, ease of use, ratiometricity, and increased NO selectivity and sensitivity compared to currently available fluorescent indicators.

Available commercial indicators (e.g., diaminofluoresceins) have been used for years but they assess NO indirectly (i.e. bind to NO oxidation products). More recently presented fluorescent probes (Cu—FL) [14] claim direct NO detection but are not ratiometric. Some very recent studies claim the development of fluorescent probes using different chemical concepts [15,16], including what is claimed to be the first ratiometric fluorescent probe for NO [16]. The disclosed complexes provide an attractive alternative due to 1) a new and unique mechanism of NO detection based on reaction with transition metal organometallic complexes, that have favorable photophysical properties and can complex NO; 2) demonstrated ratiometricity, which is ascribed to reactivity of NO with the metal complex; 3) demonstrated applicability to NO fluorescence detection in living cells, with good absorption into the cell; 4) ease of synthesis.

In various cases, the methods disclosed herein comprise contacting a sample suspected of having NO with a compound of formula (I) or (II)

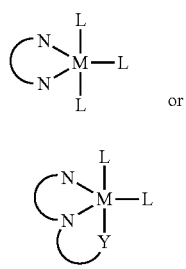

and measuring the fluorescence of the resulting mixture, wherein a change in fluorescence compared to the fluorescence of the compound of formula (I) or (II) prior to contact with the sample indicates the presence of NO in the sample, wherein M is a transition metal; each L is a ligand independently selected from CO, triflate, alkoxide, nitrate, nitrito, chloro, sulfate, amine, phosphine, phosphite, pi-bound alkene, alcohol, ketone, ether, thiol, thioether, nitrile, isonitrile, amide, thioamide or a solvent, such as THF; N—N is a bidentate nitrogen containing ligand; and N—N—Y is a tridentate nitrogen containing ligand and Y is a metal-coordinating moiety. While formulae (I) and (II) are shown in a particular orientation, it will be appreciated that any orientation of ligands about the metal are contemplated and embraced by the structures shown in formulae (I) and (II). In some cases, the compound of formula (I) or (II) can further comprise an additional L, resulting in a complex for formula (III) or (IV).

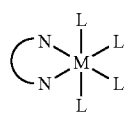

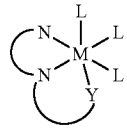

Contemplated metal-coordinating moieties include an alkene or alkyne (with pi-bond coordination to the metal) N, S, P, O (e.g., as part of a OH, $O^-$, COOH, C=O, or $COO^-$ moiety).

The bidentate ligand can comprise phenanthrolinyl, dipyridophenazinyl, or 2,2'-bipyridyl, and can be optionally substituted with a WCF, as noted above, and in some specific cases is substituted with triazolyl or dansyl. The phenanthrolinyl, dipyridophenazinyl, or 2,2'-bipyridyl can be optionally substituted with one or more moieties, such as alkyl, alkenyl, OH, $NO_2$, $CO_2H$, $NH_2$, $CO_2$alkyl, or combinations thereof.

The tridentate ligand can comprise phenanthrolinyl, dipyridophenazinyl, or 2,2'-bipyridyl substituted with a metal-coordinating moiety (e.g., N, S, P, or O, for example, as part of a OH, —O—, —N—, $O^-$, COOH, C=O, or $COO^-$ moiety), and in some cases, is substituted with a WCF as described above, or specifically dansyl or triazolyl. The tridentate ligand can further comprise one or more moieties, such as alkyl, alkenyl, OH, $NO_2$, $CO_2H$, $NH_2$, $CO_2$alkyl, alkoxide, nitrate, nitrito, chloro, sulfate, amine, phosphine, phosphite, pi-bound alkene, alcohol, ketone, ether, thiol, thioether, nitrile, isonitrile, amide, thioamide or combinations thereof.

Two prototypes have been tested. A series of tests in these probes generated by thermal or photochemical reactions have shown ratiometric fluorescent responses in solution and also NO detection on live cells by fluorescence microscopy. The disclosed complexes can be modified by chemical substitution for increased solubility in a medium (e.g., aqueous medium). Increased stability can be achieved by replacing the THF labile ligand on the metal complex with a different ligand (e.g., alkyl amines such as $Et_3N$, phosphines such as $PPh_3$) that gives more stable complexes but can also activate the complex for reaction with NO in a similar fashion as THF.

Figure 2:
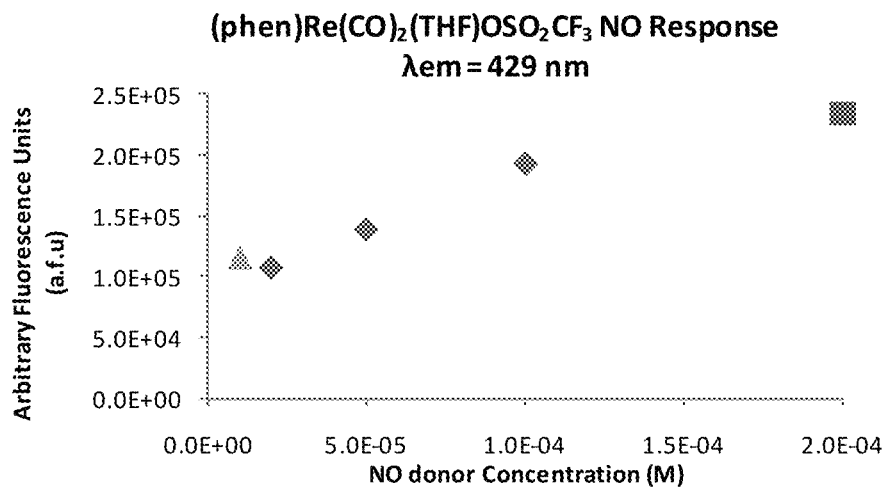
FIG. 2 shows the fluorescent response of a prototype NO sensor at $\lambda$=429 nm (intensity vs. concentration).
Figure 3:
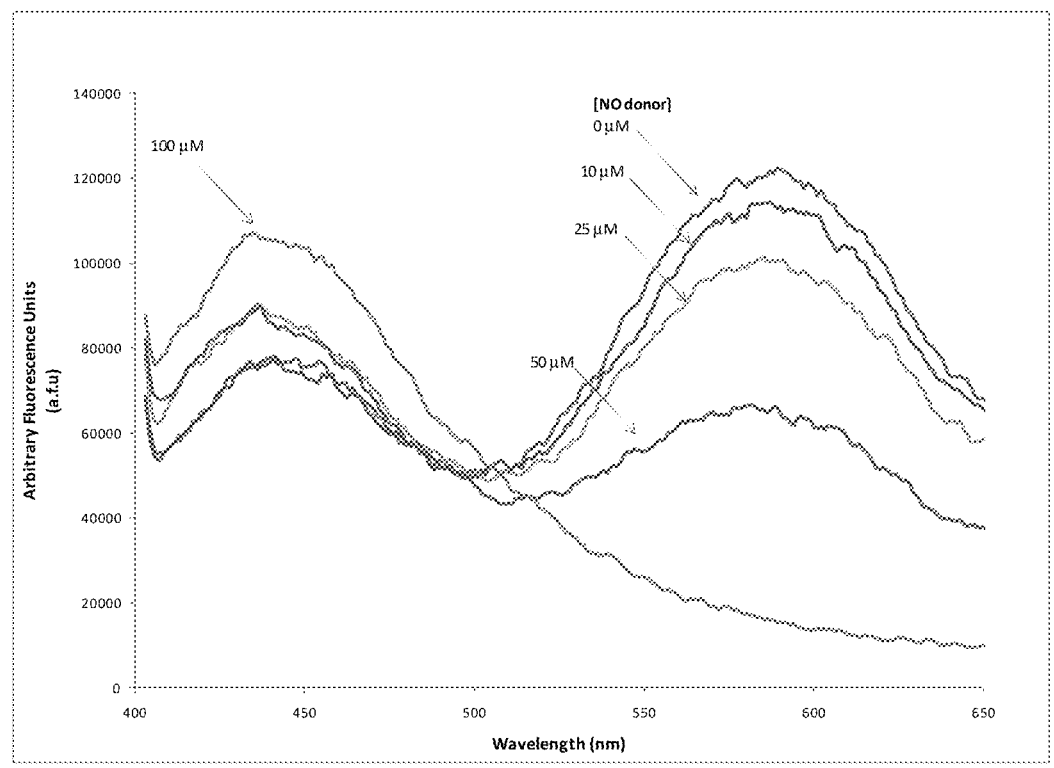
FIG. 3 shows the fluorescent response to NO-Donor addition (0-100 μM), $\lambda_{exc}$=355 nm. Re(phen)(CO)$_2$(THF)(CF$_3$SO$_3$) (40 μM) was generated by photochemical substitution (50 min).
Figure 4:
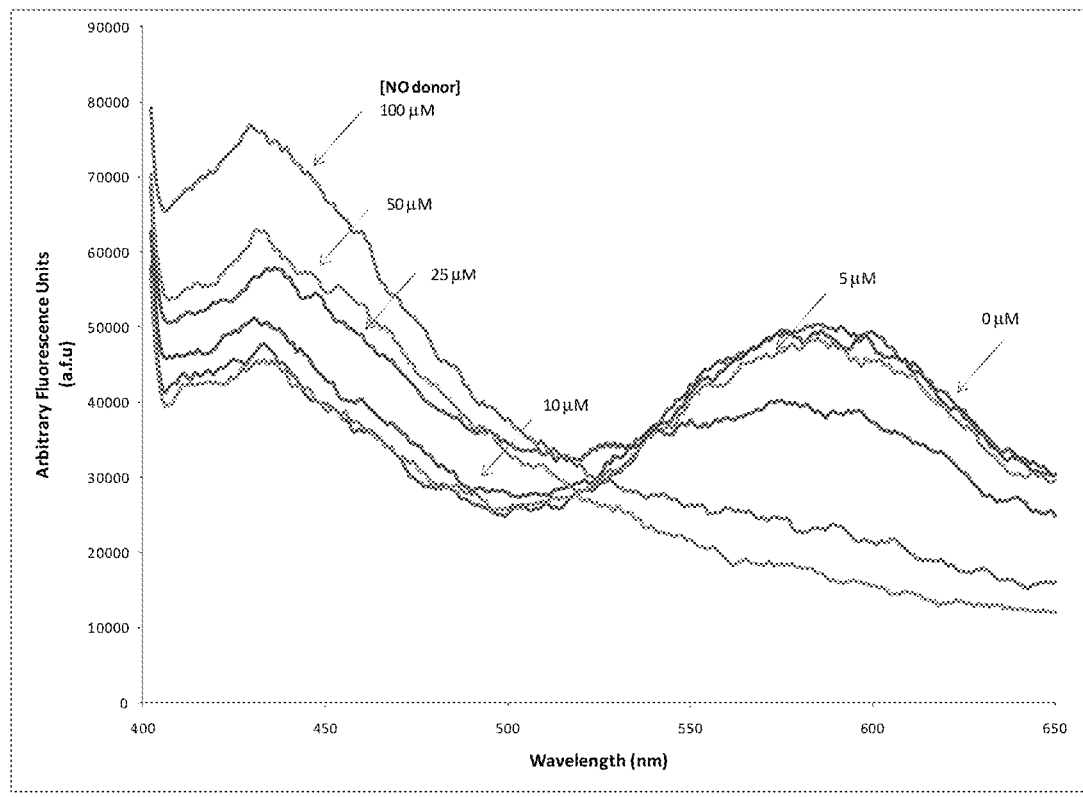
FIG. 4 shows the fluorescent response to NO-Donor addition (0-100 μM), $\lambda_{exc}$=355 nm, Re(phen)(CO)$_2$(THF)(CF$_3$SO$_3$) (20 μM) was generated by thermal substitution (24 h).
Figure 5:
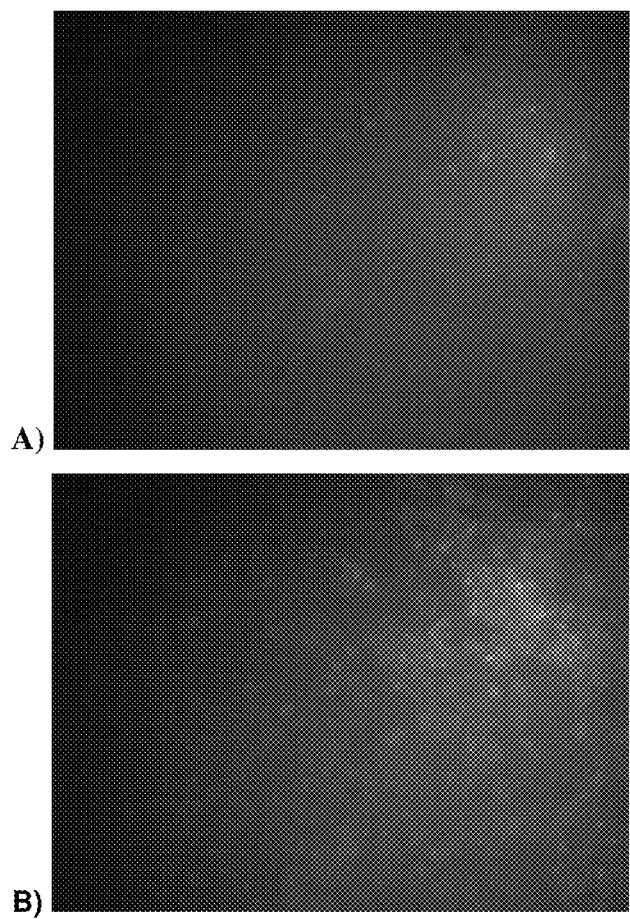
FIG. 5 shows the fluorescent response of Re(phen)(CO)$_2$(THF)(CF$_3$SO$_3$) at $\lambda$=450 nm, to NO-Donor (MAHMA-NOnoate) addition in living cells (0-10 μM). Re(phen)(CO)$_2$(THF)(CF$_3$SO$_3$) (10 μM) was generated by photochemical substitution (50 min). (a) with no NO donor added (b) with 10 μM NO donor. $\lambda_{exc}$=350 nm.
Figure 6:
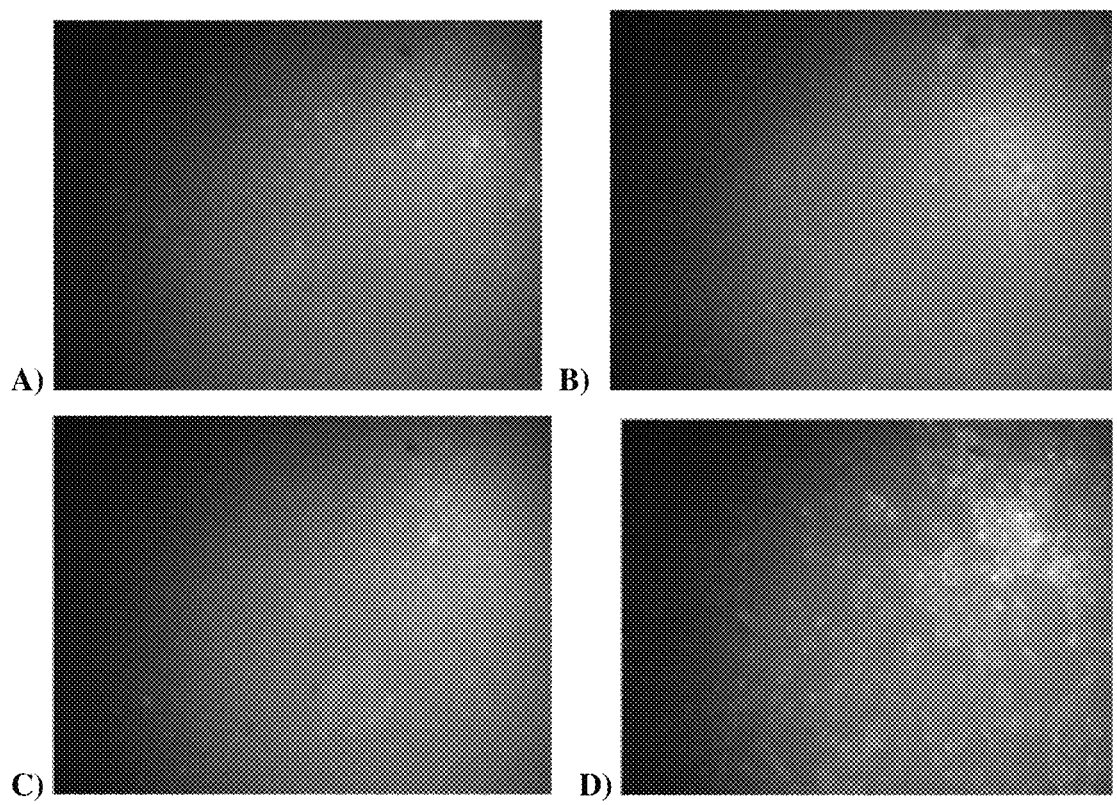
FIG. 6 shows the picture sequence demonstrating fluorescence response of Re(phen)(CO)$_2$(THF)(CF$_3$SO$_3$) (10 μM) at $\lambda_{em}$=450 nm, to NO-Donor (MAHMA-NOnoate) addition in living cells (0-10 μM), Re(phen)(CO)$_2$(THF)(CF$_3$SO$_3$) (10 μM) was generated by photochemical substitution (50 min). (a) with no NO donor added (b) with 1 μM NO donor (c) with 5 μM NO donor and (d) with 10 μM NO donor. $\lambda_{exc}$=350 nm.

A pilot Re(I)-phenanthroline complex: Re(phen)(CO)$_2$(THF)(CF$_3$SO$_3$) complex was synthesized from Re(phen)(CO)$_3$(CF$_3$SO$_3$) (Scheme 3) by photochemical substitution of a CO with THF in situ and was tested for NO sensing by fluorescence spectroscopy after the addition of the NO donor: MAHMA-NONOate (Cayman Pharmaceuticals) at the are 10 μM-200 μM range (FIGS. 1 and 2). Photochemical or thermal preparation of the complex by substitution of a CO with THF were shown to give similar results (FIGS. 3 and 4) with clear isosbestic points. Fluorescence experiments in solution with Re(phen)(CO)$_2$(THF)(CF$_3$SO$_3$) under anaerobic conditions (flushing with $N_2$ in a sealed tube) gave almost identical results with experiments under aerobic conditions, indicating that the dye responds directly to NO, rather than to NO oxidation products, which is a critical advantage for this technology. Fluorescence microscopy imaging experiments with NO donor addition in living cells (FIG. 5) show direct response, readily comparable to the solution experiments, while also demonstrating good absorptivity of the dye into the cells. It is worth mentioning the dye is highly sensitive to NO, since it is only used at a concentration of only 10 μM, and responds to concentrations of NO donor in the μM level as well (FIG. 5). It demonstrates response to NO donor addition (FIG. 6). Furthermore live cell experiments with Re(phen)(CO)$_2$(THF)(CF$_3$SO$_3$) prepared by thermal substitution gave similar results.

With regard to the mechanism of NO reactivity with the dye, current spectroscopic evidence points to direct reaction of NO to the Re metal center, with either direct ligation of a NO forming a Re-Nitrosyl species, or reaction of NO to the phen moiety, which is activated for NO attack by the presence of the "activating" THF ligand. It is unknown if the large shift in the fluorescence emission wavelength that results in ratiometric sensing is due to changes in the complex geometry and oxidation state (species 6b) or rather to a change in the overall charge of the Re complex (Species 6).

2) Preparation of a 1.0 mM stock solution of probe LRe(CO)$_3$(OSO$_2$CF$_3$) in DMSO or THF (L is phen or substituted analog). For the Re probe the solution is undergoing the following steps:
    i) 1 mL of the 1 mM LRe(CO)$_3$(OSO$_2$CF$_3$) solution is placed in a glass tube (L=phenanthroline and substituted analog). ii) The tube is irradiated at 300 nm in a refractory vessel with 6 UV lamps for 45 min.
3) A 40 mM Phosphate PBS Buffer is placed in fluorescence cuvettes.
4) The solution of step 2 is added to the buffer (to give up to 5% organic solvent in buffer).

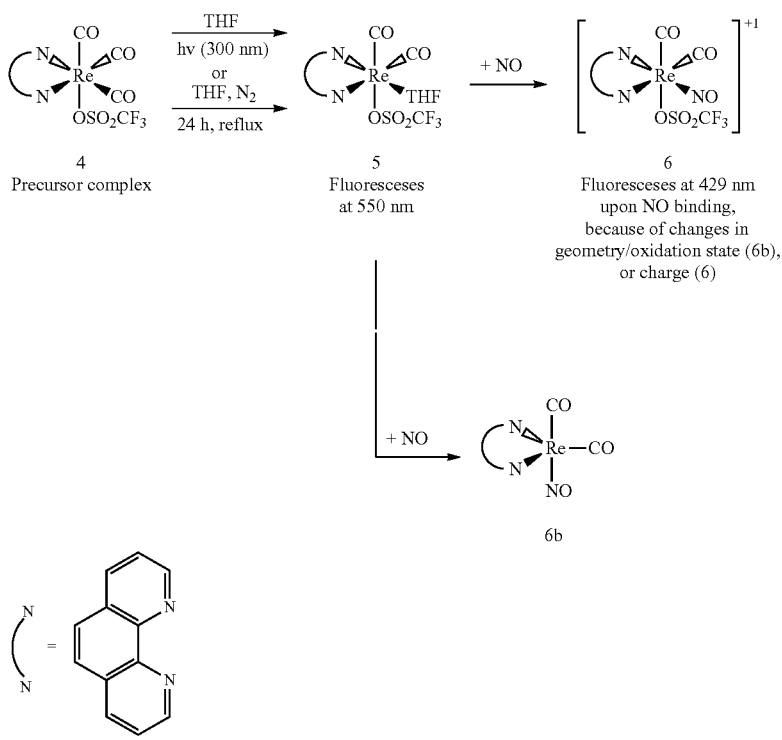

Figure 7:
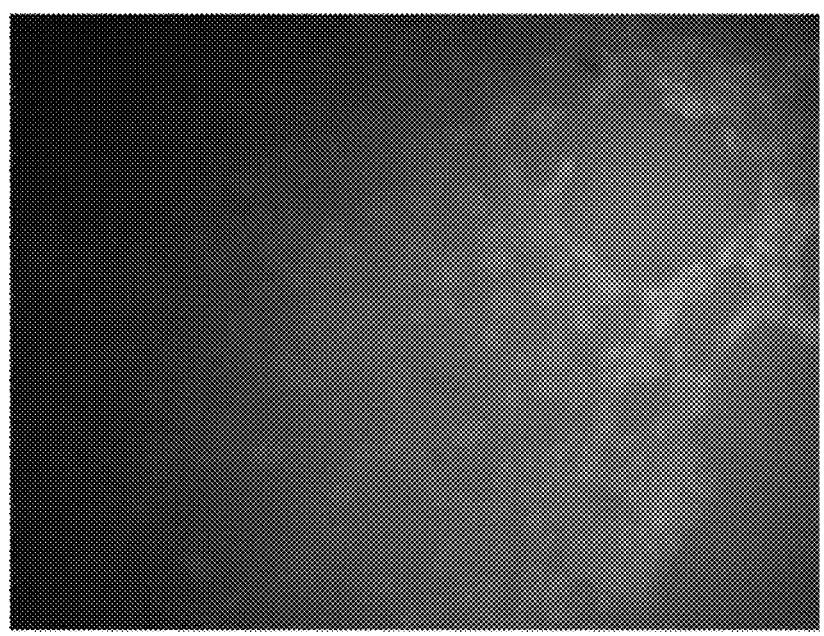
FIG. 7 shows the fluorescence emission of Re(phen)(CO)$_2$(PPh$_3$)(CF$_3$SO$_3$) at $\lambda_{em}$=450 nm, showing the absorption of the organometallic dye into living cells. Re(phen)(CO)$_2$(PPh$_3$)(CF$_3$SO$_3$) (10 μM) was prepared by thermal substitution of CO with PPh$_3$ in a tetrahydrofurane (THF) solution of Re(phen)(CO)$_3$(CF$_3$SO$_3$) and was isolated and characterized spectroscopically.

In addition to the Re(phen)(CO)$_2$(THF)(CF$_3$SO$_3$) tested both in solution and cells, a second prototype Re(phen)(CO)$_2$(PPh$_3$)(CF$_3$SO$_3$) has been synthesized and tested both in solution and in live cell experiments. This prototype has the advantage that it can be prepared thermally and be isolated in high yields and potentially commercialized in a powder form and be used with only minimal preparation. This compound also shows response to NO addition that can be ascribed to the same mechanism as for Re(phen)(CO)$_2$(THF)(CF$_3$SO$_3$). Moreover, experiments in cells with this second prototype also show good dye absorptivity into cells and no toxicity to the cells at the 10 μM level. (FIG. 7).

A stepwise experimental protocol for preparation and testing of the Rhenium organometallic sensor and comparison with existing technology is as follows:
1) Preparation of a stock solution of a 2.0 mM NO donor solution by dissolving 0.6 mg of (Z)-1-[N-Methyl-N-[6-(N-methylammoniohexyl)amino]]diazen-1-ium-1,2-diolate (Methylamine hexamethylene methylamine NONOate or MAHMA NONOate) in 0.01 M NaOH. Solution is kept at 4° C. until use.

5) The NO donor stock solution from step 1 is added in small increments in the μL range.
6) The mixed solution after each addition is shaken thoroughly by vortex.
7) The solution is left for 90 min in a sonicating bath, stirred again, and then is filtered through glasswool to ensure the absence of any non-dissolved solids that would generate scattering.
8) The fluorescence emission is measured ($\lambda_{exc}$=365 nm).

A method that will allow quantification with desired spatio-temporal resolution for the first time will be of significant interest to the broader scientific and medical community, providing a powerful tool for understanding and monitoring the NO chemistry in physiological systems, via a sensor that directly responds to NO, in a ratiometric fashion.

The immediate impact of the developed technology is expected to be a commercially available ratiometric fluorescent probe for use in biological tissues, with improved properties. The disclosed organometallic complex probes can address prior concerns by directly responding to NO, in a ratiometric fashion, and by providing a more straightforward synthetic pathway in few steps.

Some advantages of the disclosed methods lay in i) probe ratiometricity, which makes its use for NO binding, much more straightforward; ii) availability of these complexes in a few synthetic steps, as opposed to a much more complicated synthesis; and iii) the studies and data disclosed herein demonstrate the applicability to biological tissues at this stage (FIGS. 5 and 7).

EXAMPLES

Materials and Methods

Rat Aortic Endothelial Cells acquired from Cell Biologics were used for the cell based experiments. Fetal Bovine Serum (FBS) and DMSO were bought from ATCC. Penicillin-Streptomycin and endothelial cell growth supplement from bovine neural tissue were bought from Sigma Aldrich. DMEM/F-12 medium, PBS and Trypsin (0.05% EDTA) were bought from Invitrogen. Cell culture flasks and dishes were bought from Fisher Scientific. MAHMA/NO was bought from Cayman Chemicals.

Cell culture: Rat Aortic Endothelial Cells were grown (passage 4-10) in DMEM/F-12 medium supplemented with 10% FBS, 1% penicillin-streptomycin, and endothelial cell growth supplement in a humidified tissue culture incubator at 37° C. equilibrated with 95% air/5% $CO_2$. For experimentation, cells were cultured in 35×10 mm dishes seeded with $2 \times 10^5$ cells and used at 60-80% confluency.

Fluorescence NO Imaging

After the loading phase with the organometallic Re-complex (10 μM for 45 min) cells were rinsed off excess dye using PBS buffer solution. This was followed by an exposure to 10 μM MAHMA/NO for 10-15 minutes. Images were then acquired with a fluorescence microscope (Olympus IX 81 fitted with a CCD camera (Qimaging) at 350 nm (excitation) and 450 nm (emission) with 20× zoom, with exposition time of 2668 ms. The data were analyzed with IPLAB software (BioVision Technologies).

Specific Experimental Conditions for Cell Experiments:

Conditions of incubator: 37° C., 21% $O_2$, 5% $CO_2$, with cell culture harvested and plated for at least 24 hours.

Photochemical substitution occurred in a THF solution via irradiation for 1 hour at 300 nm.

Thermal substitution occurred in a THF solution, (24 h reflux, under Nitrogen gas). Photochemical and thermal substitution result in the formation of the same Re complex, which was characterized spectroscopically.

100 μM stock solution of Re(phen)(THF)(CO)$_2$(CF$_3$SO$_3$) or Re(phen)(CO)$_2$(PPh$_3$)(CF$_3$SO$_3$) ($1.6 \times 10^{-3}$ M) was prepared in THF. 62.5 μL of this solution was added to 138 μL of acetone. This new solution was added to 800 μL of 10 mM PBS (Phosphate Buffer Saline) buffer solution, resulting in v/v ratios of 6% THF, 14% acetone, and 80% Buffer. This new solution was further diluted 1/10 with PBS Buffer before added to the cells, resulting to final solvent composition of 0.6% THF, 1.4% acetone, and 98% v/v aqueous buffer. This final solution contains the organometallic Re dye at 10 μM concentration, (solution A) before contact with NO donor solutions.

A blank (0 μM NO donor: MAHMA NONOate) and 3 stock solutions (100 μM, 500 μM, 1 mM) MAHMA NONOate were prepared in NaOH 0.01M, which after addition to the media result to final NO donor concentrations of 0 μM, 1 μM, 5 μM, 10 μM.

Loading of the Re Complexes:

The old media were poured out from the plates. The plates were rinsed 2 times with 1 mL PBS 10 mM. The next reagents were added to each plate in the following order: 100 mL of DMEM/FBS/Penicillin Media, 800 mL of PBS 10 mM, and 100 μL of Re complex stock in 20% organic mixture. The plates were incubated for 75 minutes.

Loading of the MAHMA NO-NOate:

The reactive media was poured out from the plate. The plates were rinsed 2 times with 1 mL PBS 10 mM. The next reagents were added to each plate in the following order: 100 mL of DMEM/FBS/Penicillin Media, 890 μL of PBS 10 mM, and 10 μL of NO-Donor stock solution in NaOH. The plates were incubated for 15 minutes. The reactive media was poured out from the plate, and 1 mL of fresh PBS buffer solution (10 mM) was added to each plate.

REFERENCES

[1] Snyder, S. H.; Bredt, D. S. Biological roles of nitric oxide. Sci Am. 1992, 266, 68-77.

[2] Tuteja, N.; Chandra, M.; Tuteja, R.; Misra, M. Nitric Oxide as a Unique Bioactive Signaling Messenger in Physiology and Pathophysiology. J. Biomed. Biotechnol., 2004, 4, 227-237.

[3] Kojima, H.; Nakatsubo, N.; Kikuchi, K.; Kawahara, S.; Kirino, Y.; Nagoshi, H.; Hirata, Y.; Nagano, T. Detection and Imaging of Nitric Oxide with Novel Fluorescent Indicators: Diaminofluoresceins. Anal. Chem., 1998, 70, 2446-2453.

[4] Lim, M. H; Xu, D.; Lippard, S. J. Visualization of nitric oxide in living cells by a copper-based fluorescent probe. Nature Chem Biol., 2006, 2, 375-380.

[5] Kojima, H.; Urano, Y.; Kikuchi, K.; Tsunehiko, H.; Hirata, Y. Nagano, T. Fluorescent Indicators for Imaging Nitric Oxide Production. Agnew. Chem. Int. Ed. Engl., 1999, 38, 3209-3212.

[6] Tsoukias, N. M.; Popel, A. S. Erythrocyte consumption of Nitric Oxide in the presence and absence of plasma-based Hemoglobin. American Journal of Physiology 2002, 282 (6):H2265-77.

[7] Kavdia M.; Tsoukias N. M.; Popel, A. S. A model of Nitric Oxide diffusion in an arteriole: impact of hemoglobin based blood substitutes. American Journal of Physiology 2002, 282(6):H2245-53.

[8] Tsoukias, N. M.; Popel, A. S. A model of nitric oxide capillary exchange. Microcirculation 2003, 10(6): 479-95.

[9] Tsoukias, N. M.; Kavdia, M.; Popel A. S. A theoretical model of nitric oxide transport in arterioles: frequency vs amplitude dependent control of cGMP formation. American Journal of Physiology 2004, 286(3): H1043-56.

[10] Tsoukias N. M. Nitric Oxide bioavailability in the microcirculation: Insights from mathematical models. Microcirculation 2008, 15, 8.

[11] Madrasi, K.; Joshi, M. S.; Gadkari, T.; Kavallieratos, K.; Tsoukias, N. M. Glutathiyl radical as an intermediate in glutathione nitrosation Free Radical Biology and Medicine, 2012, 53, 1968-1976.

[12] Moncada, S.; Higgs, A. The L-Arginine-Nitric Oxide Pathway. N. Engl. J. Med., 1993, 329, 2002-20012.

[13] Namin, S. M.; Nofallah, S.; Joshi, M. S.; Kavallieratos, K.; Tsoukias, N. M. Kinetic Analysis of DAF-FM activation by NO; toward calibration of a NO-sensitive fluorescent dye. Nitric Oxide: Biology and Chemistry, 2013, 28, 39-46.

[14] Pluth, M. D.; McQuade, L. E.; Lippard S. J. Cell-Trappable fluorescent probes for Nitric Oxide visualization in living cells. Org. Lett. 2010, 12, 2318-2321.

[15] Hu, X.; Wang, J.; Zhu, X.; Dong, D.; Zhang, X.; Wu S.; Duan, C. A copper(II) rhodamine complex with a tripodal ligand as a highly selective fluorescence imaging agent for nitric oxide. Chem. Commun., 2011, 47, 11507-11509.

[16] Yuan, L.; Lin W.; Xie Y.; Chen B.; Song J. Development of a ratiometric fluorescent sensor for ratiometric imaging of endogenously produced nitric oxide in macrophage cells. Chem. Commun., 2011, 47, 9372-9374.

What is claimed is:

1. A method of detecting nitric oxide (NO) in a sample, comprising:

a) contacting the sample with a complex of formula (I) or formula (II):

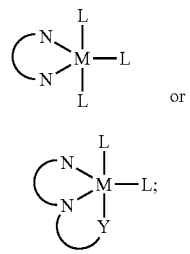

and b) measuring a fluorescence of the resulting mixture, wherein a change in fluorescence after contact with the sample, compared to the fluorescence of the complex of formula (I) or formula (II) in the absence of the sample, indicates the presence of NO in the sample, wherein M is a transition metal; each L is a ligand independently selected from the group consisting of CO, tetrahydrofuran, triflate, an alkoxide, nitrate, nitrite, chloro, sulfate, amine, phosphine, phosphite, a pi-bound alkene, an alcohol, a ketone, an ether, a thiol, a thioether, a nitrile, an isonitrile, an amide, a thioamide and a solvent; N—N is a bidentate nitrogen containing ligand; and N—N—Y is a tridentate nitrogen containing ligand and Y is a metal-coordinating moiety.

2. The method of claim 1, wherein M is selected from the group consisting of Re, Ru, Os, Ir, Mn, Tc, Fe, Ru, Co, Rh, Ni, Pd, Pt, Cu, Cr, Mo, W, V, Nb, and Ta.

3. The method of claim 2, wherein M is selected from the group consisting of Re(I), Ru(II), Os(II), and Ir(III).

4. The method of claim 1, wherein at least one L is CO.

5. The method of claim 1, wherein one L is triflate.

6. The method of claim 1, wherein one L is tetrahydrofuran.

7. The method of claim 1, wherein one L is triphenylphosphine or triethylamine.

8. The method of claim 1, wherein the bidentate ligand comprises phenanthrolinyl, dipyridophenazinyl, or bipyridyl.

9. The method of claim 8, wherein the phenathrolinyl, dipyridophenazinyl, or bipyridyl is substituted.

10. The method of claim 1, wherein the tridentate ligand comprises phenanthrolinyl, dipyridophenazinyl, or bipyridyl substituted with a metal-coordinating moiety or a weakly coordinating fluorophore ("WCF").

11. The method of claim 10, wherein the WCF is a triazolyl or a dansyl.

12. The method of claim 1, wherein the complex has a structure of formula (I) further comprising a fourth L resulting in a complex of formula (III):

13. The method of claim 1, wherein the complex has a structure of formula (II) further comprising a third L, resulting in a complex of formula (IV):

14. The method of claim 1, wherein the sample has an NO concentration of about 0.1 to about 2000 µM.

15. The method of claim 14, wherein the sample has an NO concentration of about 10 to about 200 µM.

16. The method of claim 1, wherein at least two L are CO.

17. The method of claim 1, wherein the complex is selected from the group consisting of Re(phen)(CO)$_2$(THF)(CF$_3$SO$_3$); Re(Phen)(CO)$_2$(PPh$_3$)(CF$_3$SO$_3$); and Re(phen)(CO)$_2$(Et$_3$N)(CF$_3$SO$_3$).

18. The method of claim 1, wherein the change in fluorescence is correlated to the concentration of NO in the sample.

19. The method of claim 1, wherein an emitted fluorescence intensities ratio at two wavelengths, following excitation at a third wavelength is correlated to the NO concentration in the sample.

20. The method of claim 1, wherein an emitted fluorescence intensities ratio at one wavelength, following alternate excitation at a second and third wavelength, is correlated to the NO concentration in the sample.

21. The method of claim 1, wherein measuring NO comprises at least one of detecting the presence of or determining the concentration of NO.

22. The method of claim 1, wherein the sample comprises cells and the method provides a measurement of intracellular NO concentration.

23. The method of claim 22, wherein the complex of any one of formulae (I), (II), (III) or (IV) is present in the intracellular space of the cell.

24. The method of claim 22, wherein the measurement of fluorescence intensity is an indicator of intracellular NO activity.

25. The method of claim 1, wherein the sample comprises cells and the method provides a measurement of extracellular NO concentration.

26. The method of claim 25, wherein the complex of any one of formulae (I), (II), (III) or (IV) is present in the extracellular space of the sample and the measurement of fluorescence intensity is an indicator of extracellular NO activity.

27. The method of claim 22, wherein the sample comprises cells and the method provides a measurement of NO presence in the intracellular and extracellular space of the sample.

28. The method of claim 1, wherein the measurement is carried out by using an excitation light having a wavelength of 280 nm or higher.

29. The method of claim 1, wherein the method provides measurement of an absolute concentration of NO in the sample.

* * * * *